US008636956B2

(12) United States Patent
Yamamori et al.

(10) Patent No.: US 8,636,956 B2
(45) Date of Patent: *Jan. 28, 2014

(54) SENSOR FOR MEASURING CARBON DIOXIDE IN RESPIRATORY GAS

(75) Inventors: Shinji Yamamori, Tokyo (JP); Yoshinobu Ono, Tokyo (JP); Takeshi Kojima, Tokyo (JP); Noriaki Todokoro, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 409 days.

This patent is subject to a terminal disclaimer.

(21) Appl. No.: 12/324,063

(22) Filed: Nov. 26, 2008

(65) Prior Publication Data

US 2009/0088657 A1 Apr. 2, 2009

Related U.S. Application Data

(63) Continuation of application No. 10/092,591, filed on Mar. 8, 2002, now Pat. No. 7,462,154.

(30) Foreign Application Priority Data

| Mar. 8, 2001 | (JP) | 2001-064901 |
| Apr. 5, 2001 | (JP) | 2001-107179 |
| Feb. 22, 2002 | (JP) | 2002-46480 |

(51) Int. Cl.
  *G01N 15/06* (2006.01)
(52) U.S. Cl.
  USPC ............. 422/83; 422/50; 422/400; 422/82.05

(58) Field of Classification Search
  USPC .................................. 422/83, 50, 400, 82.05
  See application file for complete search history.

(56) References Cited

U.S. PATENT DOCUMENTS

| 3,884,219 A | 5/1975 | Richardson et al. |
| 4,423,739 A | 1/1984 | Passaro et al. |
| 5,005,571 A | 4/1991 | Dietz |
| 5,095,900 A | 3/1992 | Fertig et al. |
| 5,099,836 A | 3/1992 | Rowland et al. |
| 5,282,473 A | 2/1994 | Braig et al. |
| 5,335,656 A | 8/1994 | Bowe et al. |

(Continued)

FOREIGN PATENT DOCUMENTS

| EP | 1 095 269 B1 | 6/2004 |
| JP | 49-128590 | 12/1974 |

(Continued)

*Primary Examiner* — Brian J Sines
(74) *Attorney, Agent, or Firm* — Sughrue Mion, PLLC

(57) ABSTRACT

A sensor main unit 1 is axially split into three sub-segments. A light-emitting element 2 is attached to one end portion, and a light-receiving element 3 is attached to the other end portion. A respiratory flow path 4 is formed so as to penetrate through the center portion. The sensor main unit 1 is attached to a position on the face below the nostrils, and respiratory gas from the nostrils is guided into the respiratory flow path 4 and is caused to cross over the optical axis connected the light-emitting element 2 and the light-receiving element 3, thereby measuring a carbon dioxide gas in the respiratory gas.

18 Claims, 14 Drawing Sheets

(56) References Cited

U.S. PATENT DOCUMENTS

| | | |
|---|---|---|
| 5,616,923 A | 4/1997 | Rich et al. |
| 5,666,949 A | 9/1997 | Debe et al. |
| 5,857,460 A | 1/1999 | Popitz |
| 5,957,127 A | 9/1999 | Yamamori et al. |
| 6,044,843 A | 4/2000 | O'Neil et al. |
| 6,190,327 B1 | 2/2001 | Isaacson et al. |
| 6,258,040 B1 | 7/2001 | Yamamori et al. |
| 6,379,312 B2 | 4/2002 | O'Toole |
| 6,659,962 B2 | 12/2003 | Ricciardelli |
| 7,462,154 B2 * | 12/2008 | Yamamori et al. ............ 600/532 |
| 2002/0017300 A1* | 2/2002 | Hickle et al. ............. 128/204.22 |
| 2006/0042635 A1* | 3/2006 | Niklewski et al. ....... 128/207.18 |
| 2007/0095347 A1* | 5/2007 | Lampotang et al. ..... 128/204.23 |

FOREIGN PATENT DOCUMENTS

| | | |
|---|---|---|
| JP | 62-25858 U | 2/1987 |
| JP | 63-11133 A | 1/1988 |
| JP | 64-13439 A | 1/1989 |
| JP | 2-130432 A | 5/1990 |
| JP | 5-7247 U | 2/1993 |
| JP | 5-507004 A | 10/1993 |
| JP | 8-233806 A | 9/1996 |
| JP | 2000-88741 A | 3/2000 |
| JP | 2000-312670 A | 11/2000 |
| JP | 2000-316834 A | 11/2000 |
| WO | 91/14469 A1 | 10/1991 |
| WO | 00/07498 A1 | 2/2000 |

* cited by examiner

SENSOR FOR MEASURING CARBON DIOXIDE IN RESPIRATORY GAS

CROSS-REFERENCE TO RELATED APPLICATION

This is a continuation of application Ser. No. 10/092,591 filed Mar. 8, 2002, which claims priority under 35 USC 119 from Japanese Patent Application Nos. 2001-064901, 2001-107179 and 2002-46480. The entire disclosures of the prior applications are incorporated by reference herein.

BACKGROUND OF THE INVENTION

1. Field of the Invention

The present invention relates to a sensor for measuring the concentration or presence/absence of carbon dioxide in respiratory gas through the nostrils or mouth of a living body. More particularly, the invention relates to a simple, compact sensor for measuring carbon dioxide in respiratory gas which can improve the accuracy in measurement and response.

2. Related Art

In general, when the concentration of carbon dioxide contained in respiratory gas from a living body is optically measured, the respiratory gas is caused to pass through a cylindrically-shaped airway adapter. An infrared ray is radiated onto the respiratory gas from a light-emitting element. A voltage corresponding to the amount of light which is absorbed by carbon dioxide contained in the respiratory gas is detected by a light-receiving element, thus measuring the concentration of carbon dioxide.

FIG. 16 shows the schematic configuration of an example of such a related capnometer. As shown in FIG. 16, one end 101a of an airway adapter 101—which is formed into a substantially cylindrical shape and through which respiratory gas passes—is to be connected to a tube inserted into a trachea of a patient. Another end 101b is to be connected to a Y piece of a respiratory circuit, such as a ventilator. An intermediate portion of the airway adapter 101 has a rectangular cross-sectional profile. Circular windows 101c, 101d are formed in respective, mutually-opposing surfaces of the intermediate portion such that the windows are concentrically aligned with each other. A sensor main unit 102 is removably attached to the intermediate portion of the airway adapter 101.

The sensor main unit 102 is formed into a rectangular-parallelepiped shape, and a U-shaped notch is formed in an intermediate portion of the sensor main unit 102. The intermediate portion of the airway adapter 101 is to be fittingly attached to the notch. Two mutually-opposing surfaces come into contact with the windows 101c, 101d of the airway adapter 101. A light-emitting element 103 emitting a infrared light is disposed on one side with reference to the notch formed in the sensor main unit 102.

A filter 104 for absorbing only light having wavelength to be absorbed by carbon dioxide and a light-receiving element 105 are disposed on the other side with reference to the notch formed in the sensor main unit 102. The light-emitting element 103 and the light-receiving element 105 are connected to a monitor main unit 107 via a lead wire 106. The intermediate portion of the airway adapter 101 can be removably attached to the sensor main unit 102.

In the related capnometer having the foregoing configuration, light emitted from the light-emitting element 103 enters the light-receiving element 105 by way of the window 101c, the respiratory gas in the airway adapter 101, the window 101d, and the filter 104. The quantity of light corresponding to the concentration of carbon dioxide is detected by the light-receiving element 105. An output signal from the light-receiving element 105 is input to the monitor main unit 107, where the concentration of carbon dioxide is displayed.

In the related-art example, the airway adapter 101 through which respiratory gas passes is attached to the sensor main unit 102. A related-art capnometer has a structure in which a sampling tube is connected to a sensor main unit disposed in the monitor main unit 107. In this case, one end of the sampling tube which aspirates part of respiratory gas is connected to the airway adapter 101 through which the respiratory gas passes. The other end of the sampling tube is connected to the monitor main unit 107. A pump is disposed in the monitor main unit 107, and respiratory gas is led to the sensor main unit disposed in the monitor main unit 107.

U.S. Pat. Nos. 5,099,836 and 5,335,656 describe other types of related respiratory gas sensors. U.S. Pat. No. 5,099,836 shows a partially cutaway top view shown in FIG. 17. As shown in FIG. 17, the inside of a tubular nasal cannula 201 is separated into a first separate chamber 203 and a second separate chamber 204 by a wall 202. One end of the wall 202 is connected to one side of an interior surface of the nasal cannula 201, and the other end of the same is connected to the other side of the interior surface, thus hermetically separating the two separate chambers 203, 204 from each other. Nasal tubes 205, 206 to be inserted into respective nostrils project in parallel with each other from an outer periphery of the nasal cannula 201. The inside of the nasal tube 205 is separated into passageways 205a, 205b by the wall 202 extending from the inside of the nasal cannula 201. Similarly, the inside of the nasal tube 206 is separated into passageways 206a, 206b by the wall 202. The passageways 205a, 206a are in communication with the first separate chamber 203, and the passageways 205b, 206b are in communication with the second separate chamber 204.

An oxygen gas supply tube 207 is connected to one end of the first separate chamber 203 of the nasal cannula 201. A tubing 208 is connected to one end of the second separate chamber 204 for sensing the user's breathing pressure. An oxygen cylinder is connected to the tube 207 through a pressure control valve (not shown). The tubing 208 is connected to a pressure transducer (not shown).

There may be a case where the tubing 208 is used as a sampling tube and connected to a carbon dioxide sensing monitor (not shown) to measure the concentration of carbon dioxide in respiratory gas.

In relation to the apparatus for detecting respiratory gas configured in the manner as mentioned above, the oxygen supplied from the oxygen cylinder through the tube 207 is fed to the nostrils through the first separate chamber 203, the passageway 205a of the nasal tube 205, and the passageway 206a of the nasal tube 206. Part of exhaled gas from the nostrils is discharged to the tubing 208 through the passageway 205b, 206b and the second separate chamber 204, and the breathing pressure and the concentration of carbon dioxide are detected.

As shown in FIG. 18, U.S. Pat. No. 5,335,656 relates to a nasal cannulae 301 which has a tubular body, is to be attached to the skin in the vicinity of the nose, supplies a treating gas to the nostrils, and measures the concentration of carbon dioxide in respiratory gas. A septum 302 is disposed in the nasal cannulae 301 to define an inhalation manifold 303 and an exhalation manifold 304. A flexible tubing segment 305 is connected to one end of the nasal cannulae 301 for supplying a treating gas to the inhalation manifold 303. A flexible tube segment 306 is connected to the other end of the nasal cannulae 301 for aspirating the exhaled gas from the exhalation manifold 304.

A nasal prong 307 is connected to the inhalation manifold 303 for supplying the gas to a first nostril. The exhalation manifold 304 is connected to and is communicated with a nasal prong 308 which is fitted to a second nostril to aspirate the exhaled gas. The segment 306 is connected to a carbon dioxide measurement sensor (not shown) which measures the partial pressure of carbon dioxide in the exhaled gas.

The related capnometer shown in FIG. 16 requires the airway adapter 101. The airway adapter 101 is connected to an endotracheal tube and a Y piece. Hence, difficulty is encountered in connecting the apparatus to a patient to whom no endotracheal tube is attached. Further, the apparatus is bulky, expensive, and complicated in construction. Further, the airway adapter 101 must be replaced, thus increasing operating costs. The light-emitting element 103 has hitherto involved power consumption of 1 W or more. Hence, the sensor main unit 102 becomes hot. If the apparatus is designed so as to come into direct contact with the skin, the apparatus will remain in contact with the skin for a long period of time for measurement, thus posing a risk of heat injury.

When the tubing shown in FIG. 17 is used, there arises a problem of the tubing is clogged with moisture in respiratory gas after long-term use. Further, the detection tube is disposable, thereby adding to operating costs. When the tubing is used as a sampling tube, there arises a time lag until the time carbon dioxide gas is detected, because the length of the tubing is usually 2 meters or more. Hence, detecting response becomes slow, which in turn deteriorates detection accuracy.

According to the related-art example shown in FIG. 17, if one of the pair of nostrils into which the nasal tubes 205, 206 are inserted has been clogged, the tube inserted in the thus-clogged nostril comes to sample air. The concentration of carbon dioxide gas in a sampled respiratory gas becomes about one-half the actual concentration in respiratory gas, which in turn may cause an error in measurement. Further, in the related-art example shown in FIG. 18, if the nostril into which the nasal prong 307 of the inhalation manifold 303 is inserted has been clogged, a treating gas cannot be supplied to a living body. In contrast, if the nostril into which the nasal prong 308 of the exhalation manifold 304 is inserted has been clogged, detection of carbon oxide gas becomes impossible.

SUMMARY OF THE INVENTION

The present invention has been conceived against such a problem and aims at providing a compact, inexpensive sensor for measuring carbon dioxide gas in a respiratory gas which can accurately detect the concentration of carbon dioxide gas even when one of a pair of nostrils has been clogged, improve measurement accuracy and responsibility, and curtail operating costs.

In order to achieve the object, there is provided a sensor for measuring the concentration or presence/absence of carbon dioxide in respiratory gas from a living body, comprising:

a support member for supporting a light-emitting element and a light-receiving element which are disposed on a single optical axis so as to oppose each other; and a respiratory flow path formed in the support member in such a manner that the respiratory gas can flow so as to cross over the optical axis when the support member is attached to an area located below the nostrils of the living body.

In the present invention, the sensor further comprises retaining means for attaching and securing the support member to a position below the nostrils.

In the present invention, retaining means corresponds to ear straps which are hooked around the ears of the living body for holding.

In the present invention, the ear straps includes at least one of a first lead wire for supplying power to the light-emitting element and a second lead wire for outputting a signal detected by the light-receiving element to the outside such that at least one of first and second lead wire is laid in the ear straps.

In the present invention, the retaining means corresponds to an engagement member provided on the support member and engaged with a tubular member for supplying oxygen to the nostrils.

In the present invention, the retaining means is an oxygen mask which covers the face of the living body and supplies oxygen.

In the present invention, the support member is provided with a respiratory guide section for guiding the respiratory gas from the nostrils to the respiratory flow path.

In the present invention, the support member is provided with an adapter having nasal prongs to be inserted into the nostrils for introducing the respiratory gas from the nostrils to the respiratory flow path.

In the present invention, the support member is provided with a respiratory guide section for introducing the respiratory gas from the mouth to the respiratory flow path.

In the present invention, there is provided a sensor for measuring the concentration or presence/absence of carbon dioxide in gas respiratory from a living body, comprising:

a support member for supporting a light-emitting element and a light-receiving element which are disposed on a single optical axis so as to oppose each other;

a respiratory flow path formed in the support member in such a manner that the respiratory gas can flow so as to cross over the optical axis; and an oxygen mask covering the face of the living body and supplies oxygen, wherein the support member is provided on an exterior surface of the oxygen mask to bring the inside of the oxygen mask in communication with the respiratory flow path.

In the present invention, the light-emitting element is a miniature infrared radiation lamp having a power consumption of 0.3 W or less.

In the present invention, there is provided a sensor for measuring the concentration or presence/absence of carbon dioxide in respiratory gas from a living body, comprising:

an airway case opened on both ends thereof and having at least a circumferential wall having a hole formed therein for passing through the respiratory gas; and a pair of holding members for hermetically holding transparent thin films between respective end faces of the airway case;

a pair of supporting members respectively fitted into the outer end faces of the pair of holding members, for supporting a light-emitting element and a light-receiving element which are disposed on a single optical axis so as to oppose each other, wherein the airway case is attached to a position below the nostrils of the living body, the respiratory gas can cross over the optical axis.

In the present invention the thin films are anti-fogging films for preventing condensation of moisture in the respiratory gas on the surfaces of the films.

In the present invention, a pair of supporting members are removably engaged with a pair of holding members through engagement members.

In the present invention, the airway case is provided with an adapter having nasal prongs to be inserted into the nostrils for introducing respirator gas from the nostrils into the airway case.

In the present invention the airway case has a respiratory guide section for introducing respiratory gas from the mouth into the airway case.

According to the present invention, there is provided a respiratory gas from a living body can be guided directly to an optical axis of a sensor through a respiratory flow path provided in the sensor. Hence, there is obviated a necessity for an airway adapter and a sampling tube, which have hitherto been employed, thereby rendering the sensor compact and less expensive. Even if one of the nostrils becomes clogged, the concentration of carbon dioxide gas can be detected accurately, thereby improving measurement accuracy and responsibility.

According to the present inventions, a cylindrical member through which respiratory gas flows and a support member for supporting a light-emitting element and a light-receiving element are formed separately and removably from each other. Hence, production of a cylindrical member is facilitated, as is cleaning of the cylindrical member. Moreover, thin films are hermetically interposed between the cylindrical member and the support member by holding members. Hence, so long as the thin films are formed from a anti-fogging film, occurrence of clouding due to moisture in respiratory gas can be prevented, thereby enabling accurate measurement of concentration of carbon dioxide gas in the respiratory gas.

DETAILED DESCRIPTION OF PREFERRED EMBODIMENTS

Embodiments of a sensor for measuring the concentration of a carbon dioxide gas in respiratory gas according to the invention will be described herein below by reference to the accompanying drawings.

Figure 1:
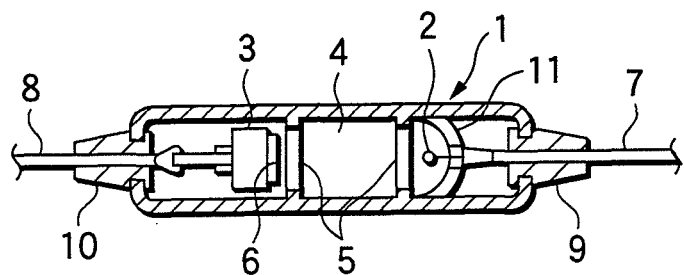
FIG. 1 is a transverse cross-sectional view showing an example configuration of a sensor for measuring the concentration of a carbon dioxide in respiratory gas according to a first invention.

FIG. 1 is a transverse cross-sectional view showing an example configuration of a sensor according to a first invention. As shown in FIG. 1, a sensor main unit 1 which is formed from resin or metal into a substantially cylindrical shape and serves as a support member is axially separated into three chambers. A light-emitting element 2 is disposed in a chamber located at one end of the three chambers, and a light-receiving element 3 is disposed in another chamber located at the other end of the three chambers. An respiratory flow path 4 is formed so as to vertically penetrate a middle chamber of the three chambers. The respiratory flow path 4 is hermetically separated from the adjacent two chambers by partitions. An opening section is formed in each of the partitions. A transparent window 5 which permits transmission of light is hermetically fitted to the opening section formed in the chamber having the light-emitting element 2 provided therein and to the opening section formed in the chamber having the light-receiving element 3 provided therein. A filter 6 which permits transmission of only light having a wavelength to be absorbed by a carbon dioxide gas is provided on the light-receiving element 3.

A lead wire 7 is connected to the light-emitting element 2 for supplying voltage. A lead wire 8 is connected to the light-receiving element 3 for extracting a detected signal to the outside. The lead wire 7 is retained by the sensor main unit 1 through a socket 9, and the lead wire 8 is retained by the sensor main unit 1 via a socket 10. The light-emitting element 2 is constituted of a miniature lamp which radiates infrared rays with power consumption of 0.3 W or less.

Figure 2A:
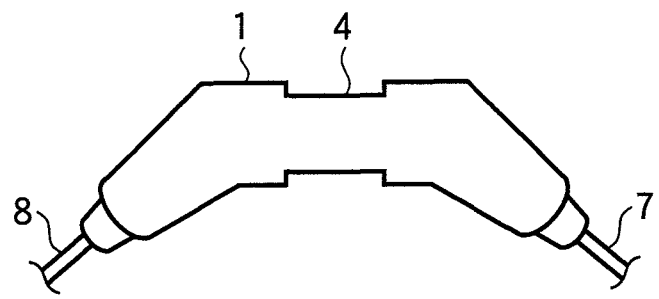
FIG. 2A is a perspective view showing an overview of one configuration example of a sensor main unit.
Figure 2B:
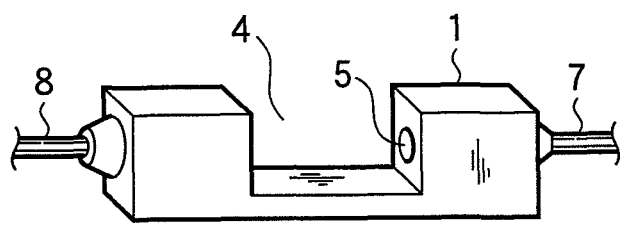
FIG. 2B is a perspective view showing an overview of another configuration example of the sensor main unit.
Figure 2C:
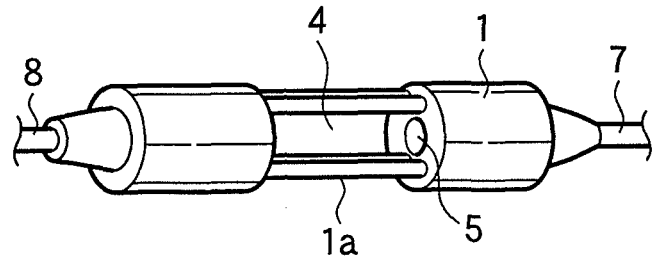
FIG. 2C is a perspective view showing an overview of yet another configuration example of the sensor main unit.

FIGS. 2A through 2C show another example configurations of the sensor main unit 1 shown in FIG. 1. FIG. 2A shows an example in which both ends of the sensor main unit 1 are bent so as to match the contour of part of the face located below nostrils of a living body. Even in this case, the light-emitting element 2 and the light-receiving element 3 are aligned with a single optical axis, spaced a given distance from each other, and secured to and retained on the sensor main unit 1. In this example, the sensor main unit 1 can be stably retained on the face of the living body.

FIG. 2B shows an example in which the sensor main unit 1 is formed into a rectangular-parallelepiped, the respiratory flow path 4 provided by cutting off the axial center of the rectangular parallelepiped. Here, the sensor main unit 1 may be cylindrical.

FIG. 2C shows an example of the sensor main unit 1: that is, the end section having the light-emitting element 2 housed therein and the end section having the light-receiving element 3 housed therein, are connected together by a plurality of connecting rods: e.g., four connecting rods 1a. In this configuration, even if respiratory gas crosses over an optical path between the light-emitting element 2 and the light-receiving element 3 at substantially any angles, measurement of the respiratory gas can be effected. Hence, so long as an optical path is orthogonal to the flow of the respiratory gas, there is increased the area for positioning the sensor main unit 1 to be attached below the nostrils.

Figure 3:
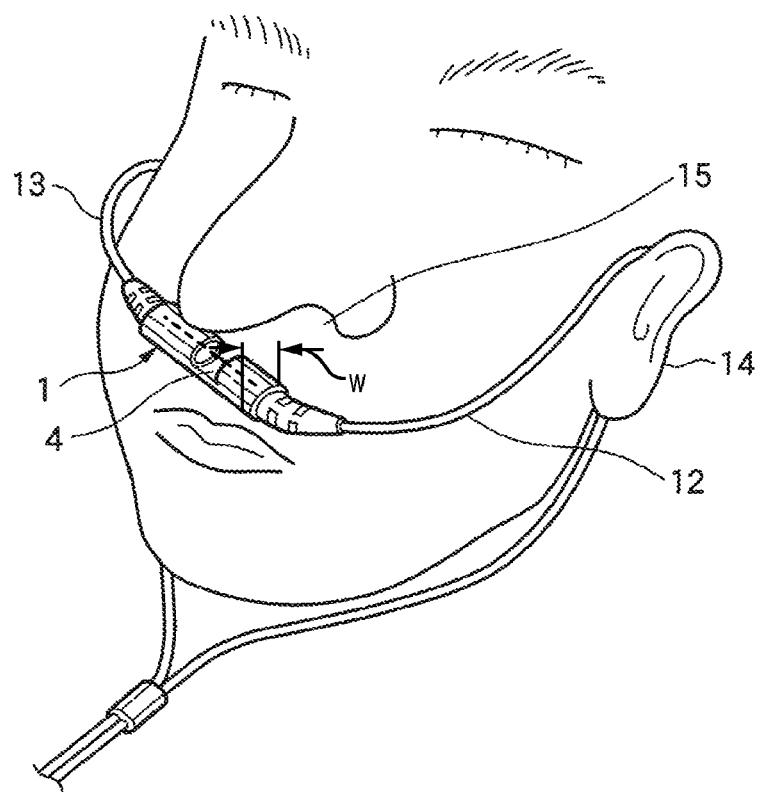
FIG. 3 is a perspective view showing the sensor main unit shown in FIG. 1 when the unit is fastened by ears by way of ear straps.

Next will be described retaining means for retaining the sensor main unit 1 constructed in the manner mentioned above to a position located below the nostrils of the face of a subject. FIG. 3 is a perspective view showing a first example configuration of the retaining means. Ear straps 12, 13 are connected to the respective ends of the sensor main unit 1. The lead wire 7 or 8 is embedded in one of the ear straps 12, 13, and the remaining lead wire is embedded in the remaining year strap. Hooking the ear straps 12, 13 around ears 14, the sensor main unit 1 is retained in a position located below the nostrils 15. The width (w) of the support member in a direction perpendicular to a line (dashed line) extending between the light-emitting element and the light-receiving element is smaller than a distance between the nostrils and the mouth.

Figure 4:
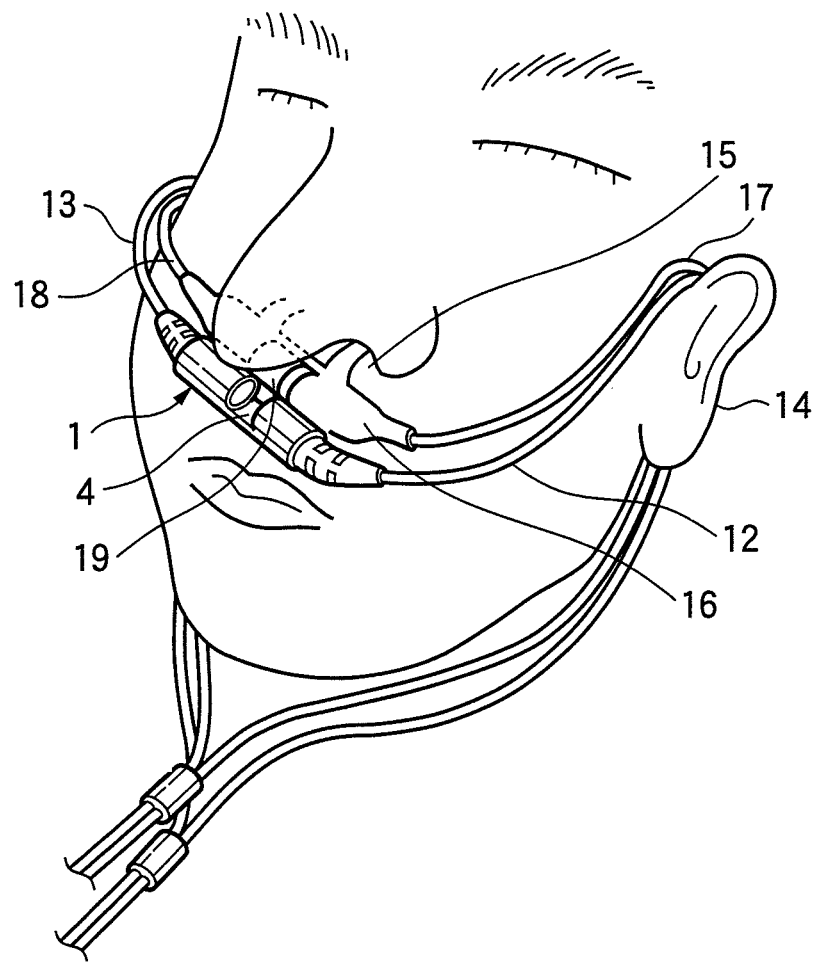
FIG. 4 is a perspective view showing the sensor main unit shown in FIG. 1 when the unit is attached to a nasal tube.

FIG. 4 is a perspective view showing a second example configuration of the retaining means. A nasal tube 16 which is a tubular member for supplying oxygen into the living body is inserted into the nostrils 15 of the subject. Tubes 17, 18 are connected to the respective ends of the nasal tube 16 for supplying oxygen. A U-shaped grip 19 serving as an engagement member is formed integrally with an outer peripheral surface of the center portion of the sensor main unit 1 so as to project to the outside.

In this configuration, as a result that the grip 19 of the sensor main unit 1 is fitted to the outer circumferential surface of the nasal tube 16, the sensor main unit 1 can be attached to and retained on a position below the nostrils 15 of the subject. At this time, the tubes 17, 18 of the nasal tube 16 are put around the ears 14 of the subject. As shown in FIG. 4, if the ear straps 12, 13 of the sensor main unit 1 are hooked around the ears 14, the sensor main unit 1 can be retained more reliably. In this state, respiratory gas from the nostrils 15 is introduced into the respiratory flow path 4 of the sensor main unit 1. The sensor main unit 1 can detect the concentration or presence/absence of a carbon dioxide gas.

Figure 5:
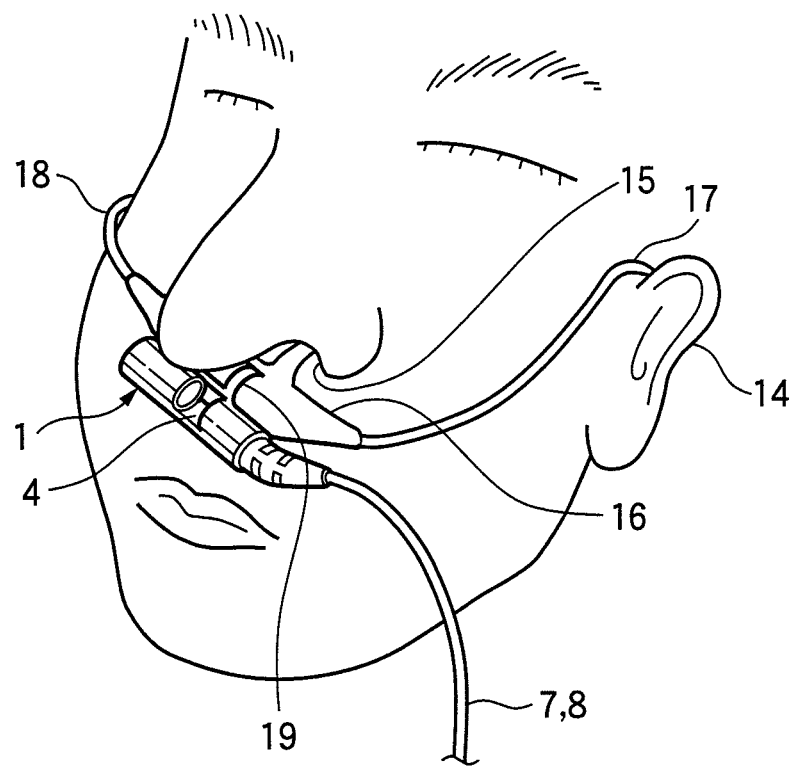
FIG. 5 is a perspective view showing a state in which lead wires embedded in the ear straps shown in FIG. 4 are bundled into one side of the sensor main unit.

As shown in FIG. 4, there has been described a case where the ear straps 12, 13 having the lead wires 7, 8 embedded therein are connected to the respective ends of the sensor main unit 1. As shown in FIG. 5, the lead wires 7, 8 may be bundled into a single wire and may not be put around the ear 14. In this case, the sensor main unit 1 is retained by the nasal tube 16 by way of the grip 19.

In place of using the ear straps 12, 13 shown in FIG. 3, a tape may be used as retaining means for retaining the sensor unit 1 on the face of the subject.

Figure 6:
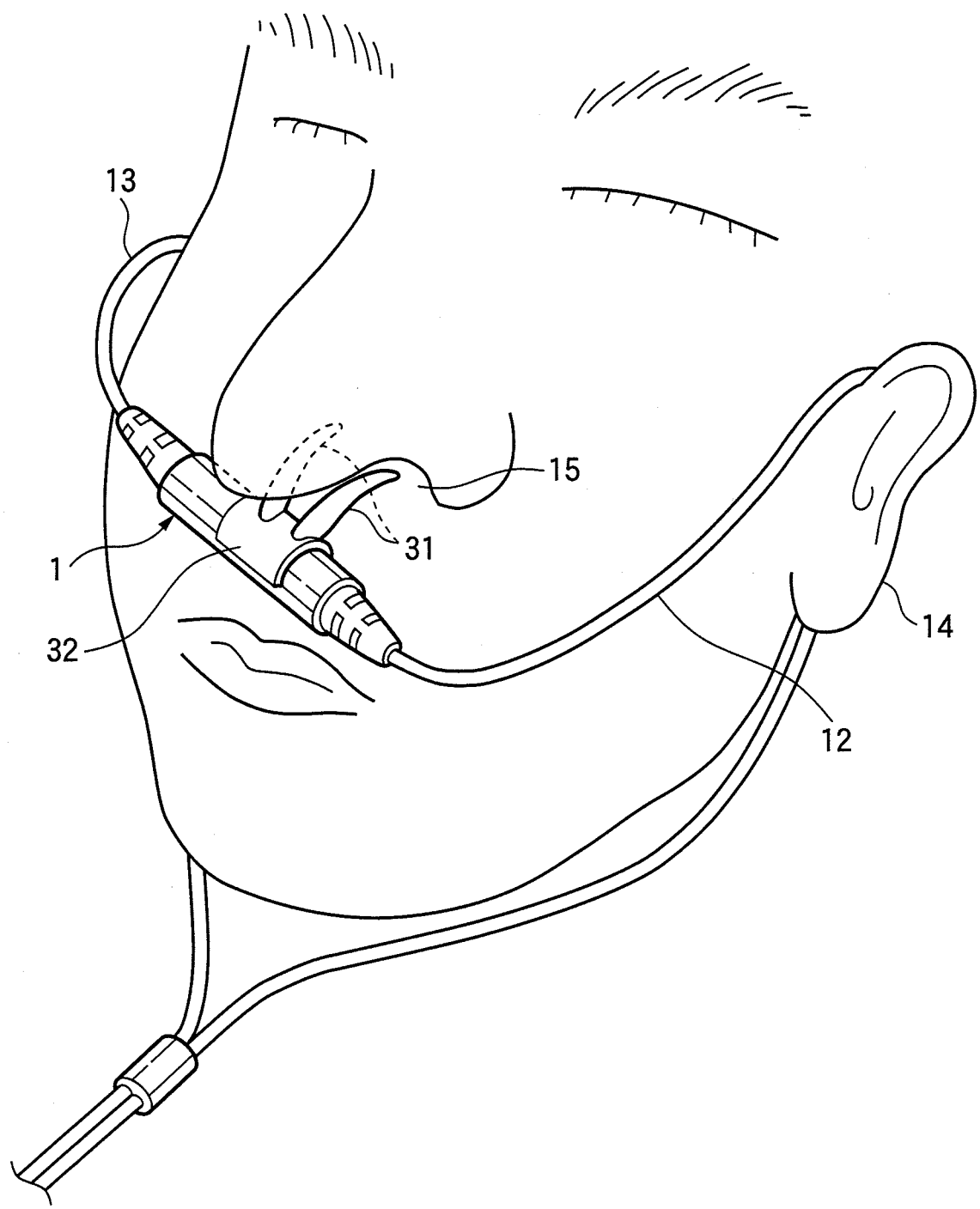
FIG. 6 is a perspective view showing a state in which an adapter having nasal prongs is attached to an outer peripheral surface of the sensor main unit shown in FIG. 3.
Figure 7A:
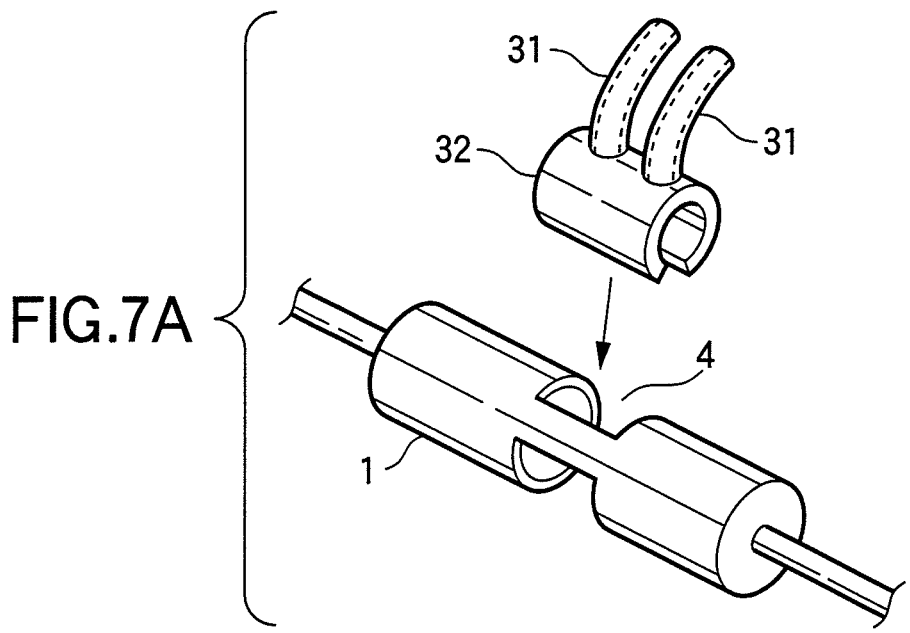
FIG. 7A is an exploded perspective view showing the principal features of the sensor main unit shown in FIG. 6.
Figure 7B:
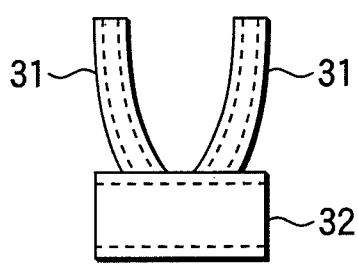
FIG. 7B is a front view showing an example of another geometry of the nasal prongs shown in FIG. 6.
Figure 7C:
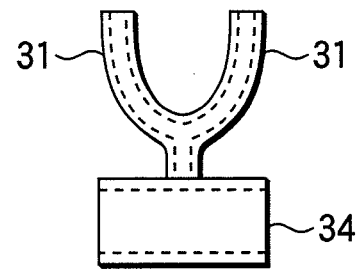
FIG. 7C is a front view showing an example of yet another geometry of the nasal prongs shown in FIG. 6.
Figure 7D:
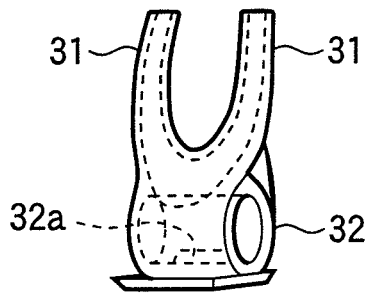
FIG. 7D is a perspective view showing an another example of configuration of the adapter shown in FIG. 6.
Figure 7E:
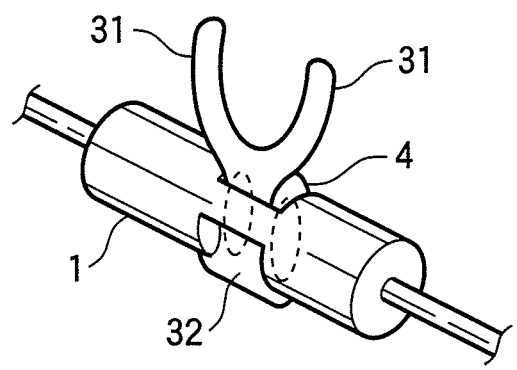
FIG. 7E is an exploded view showing the adapter when it is fitted into the sensor main unit shown in FIG. 7D.

As the perspective view shown in FIG. 6, the outer peripheral surface of the respiratory flow path 4 formed in the sensor main unit 1 is covered with a semi-cylindrical adapter 32 having a pair of nasal insertion prongs 31. In this case, as shown in an exploded perspective view shown in FIG. 7A, the nasal prongs 31 communicate with the inside of the adapter 32, and the respiratory gas from the nose is guided to the respiratory flow path 4 of the sensor main unit 1. As shown in FIG. 7A, the pair of nasal prongs 31 may be separated from each other. Alternatively, as shown in FIG. 7B, the shape of nasal prongs 31 may be letter V. Further, as shown in FIG. 7C, the shape of nasal prongs 31 may be letter U. Further, as can be seen from a perspective view shown in FIG. 7D, the adapter 32 may be formed into a substantially-cylindrical shape. As can be seen from a perspective view shown in FIG. 7E, the adapter 32 may be inserted into the respiratory flow path 4 of the sensor main unit 1. In this case, an opening section 32a is formed in the bottom of the adapter 32 for circulation of respiratory gas.

Figure 8:
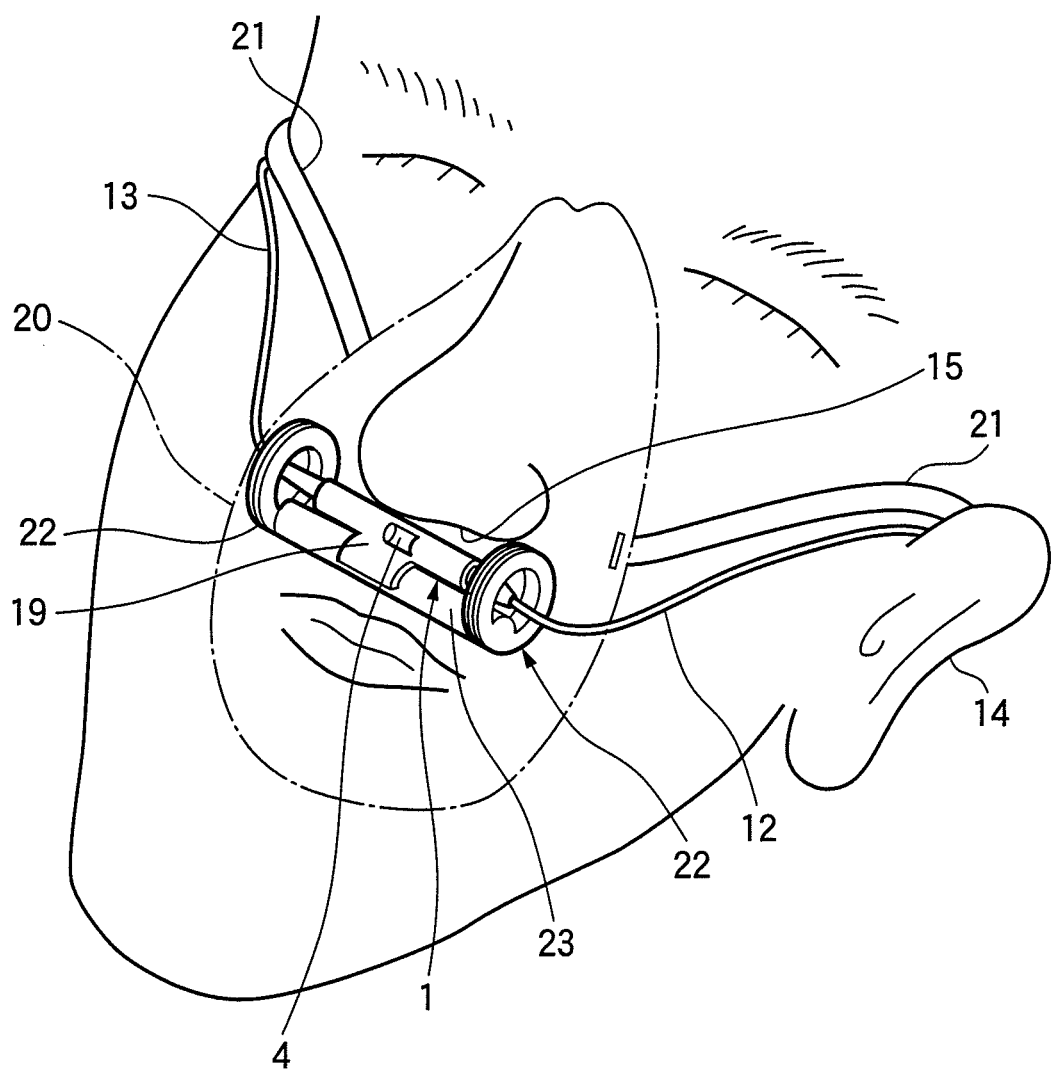
FIG. 8 is a perspective view showing an example of configuration of an example of a sensor for measuring the concentration of a carbon dioxide in respiratory gas according to the second invention.

FIG. 8 is a perspective view showing an example configuration of the second embodiment of the invention. In this example, the sensor main unit 1 is attached to and retained on an interior surface of an oxygen mask 20 attached to the face. As shown in FIG. 8, the oxygen mask 20 is fastened around the ears 14 by bands 21. A pair of annular adapters 22 are secured on positions below the nostrils 15 in the oxygen mask 20 so as to oppose each other. The adapters 22 are jointed together by a connecting rod 23. The grip 19 provided on the sensor main unit 1 is fitted to the connecting rod 23 so that the sensor main unit 1 is retained in the oxygen mask 20. At this time, the ear straps 12, 13 connected to the sensor main unit 1 are fastened around the ears 14.

Even the present example yields the same operation and working effect as those yielded in the first example shown in FIG. 3.

Figure 9:
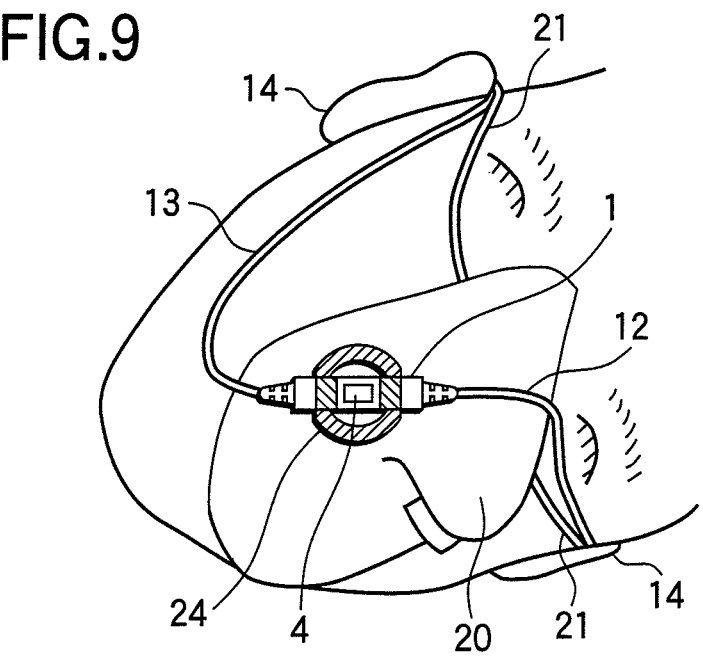
FIG. 9 is a perspective view showing the sensor main unit shown in FIG. 1 when the sensor main unit is attached to an exterior surface of an oxygen mask.

FIG. 9 is a perspective view showing a fourth example of the retaining means. In this example, the sensor main unit 1 is attached to and retained on the exterior surface of the oxygen mask 20 attached to the face. As shown in FIG. 9, the sensor main unit 1 is fixed to a position on the exterior surface of the oxygen mask 20 where a respiratory hole is to be formed, by way of an annular adapter 24. The sensor main unit 1 measures a carbon dioxide gas in the respiratory gas from the oxygen mask 20.

Even the present example yields the same operation and working effect as those yielded in the first example shown in FIG. 3.

Figure 10:
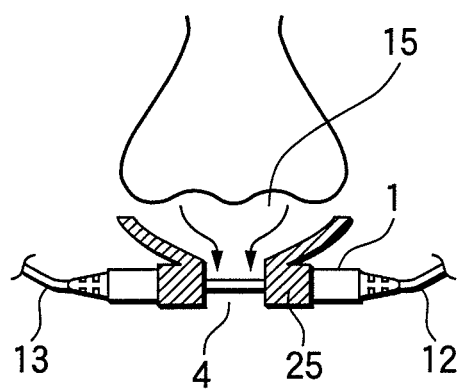
FIG. 10 is a partially cutaway front view showing an respiratory gas inlet guide when provided at the entrance of a respiratory flow path of the sensor main unit shown in FIG. 1.

FIG. 10 is a partially cutaway front view showing an example in which a respiratory guide section 25 is provided at the entrance of the respiratory flow path 4 of the sensor main unit 1 for guiding exhaled gas to the respiratory flow path 4. The respiratory guide section 25 has the shape of a funnel which can be brought into intimate contact with an area of the face located below the nose.

In the example, a respiratory gas can be introduced into the respiratory flow path 4 without fail. Even if one of the nostrils 15 has been clogged, a carbon dioxide gas in the respiratory gas can be detected without fail.

Figure 11:
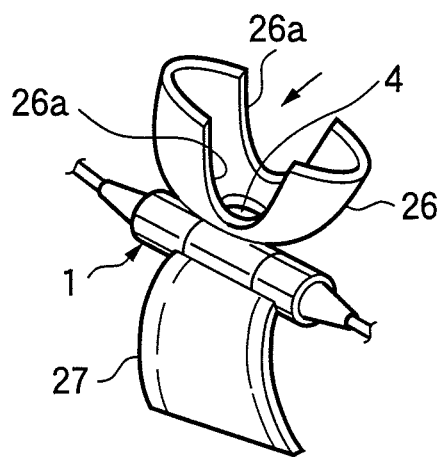
FIG. 11 is a perspective view showing an air guide for nasal respiration and an air guide for oral respiration provided in the respiratory gas inlet guide shown in FIG. 10.

FIG. 11 is a perspective view showing another example configuration of the respiratory guide section. In the example, an air guide for nasal respiration 26 and an air guide for oral respiration 27 are fixed to the outer periphery of the respiratory flow path 4 of the sensor main unit 1. The air guide for nasal respiration 26 has the shape of a funnel, and notches 26a are formed in the center positions of respective sides of the air guide 26, thus enabling insertion of the nose. The notch 26a may be formed in one side of the air guide 26 facing the living body, and there may be obviated a necessity for forming the notch 26a in the other side. Depending on the height of the air guide for nasal respiration 26, the notches 26a formed in both sides of the guide section may be obviated.

The air guide for oral respiration 27 is situated so as to oppose the mouth when the sensor main unit 1 is attached to the face and is formed into a plate warped toward the mouth. Alternatively, only either the air guide for nasal respiration 26 or the air guide for oral respiration 27 may be provided on the sensor main unit 1.

Figure 12:
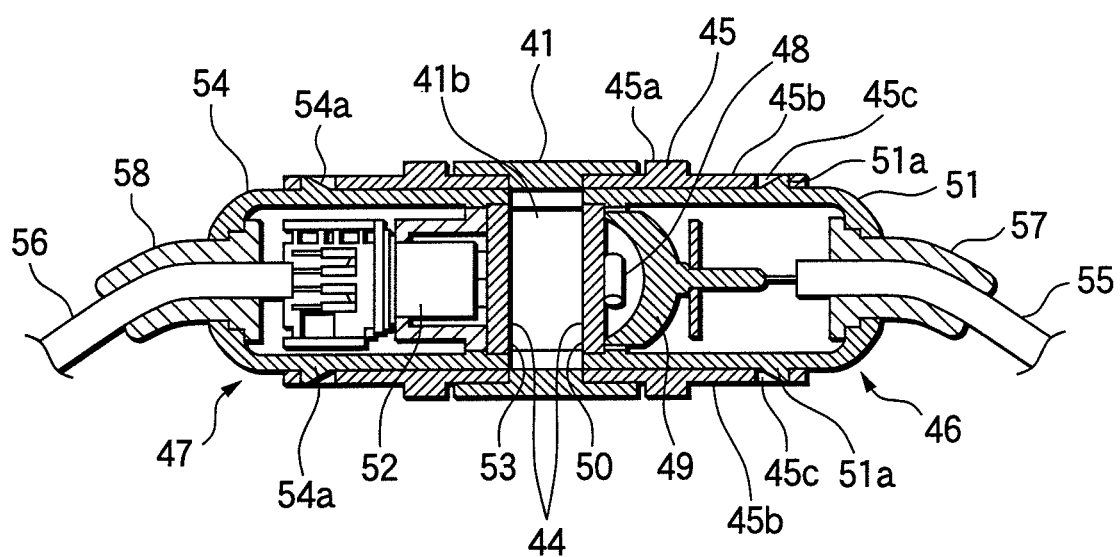
FIG. 12 is a transverse cross-sectional view showing an example configuration of the third invention.
Figure 13:
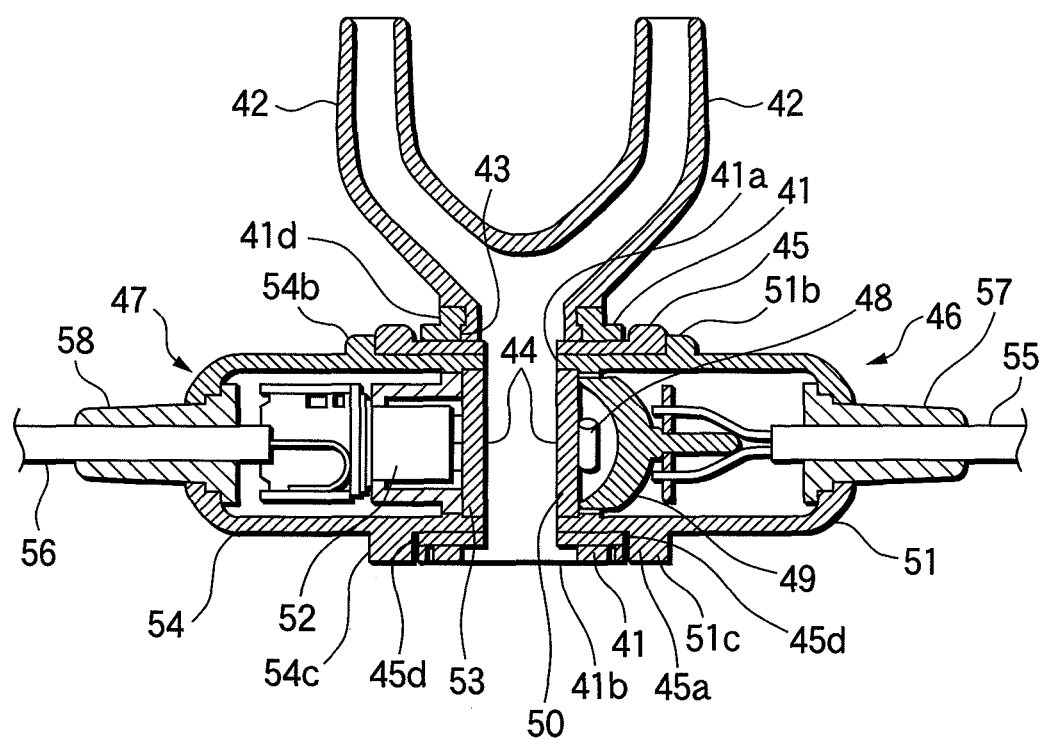
FIG. 13 is a longitudinal cross-sectional view shown in FIG. 12.
Figure 14:
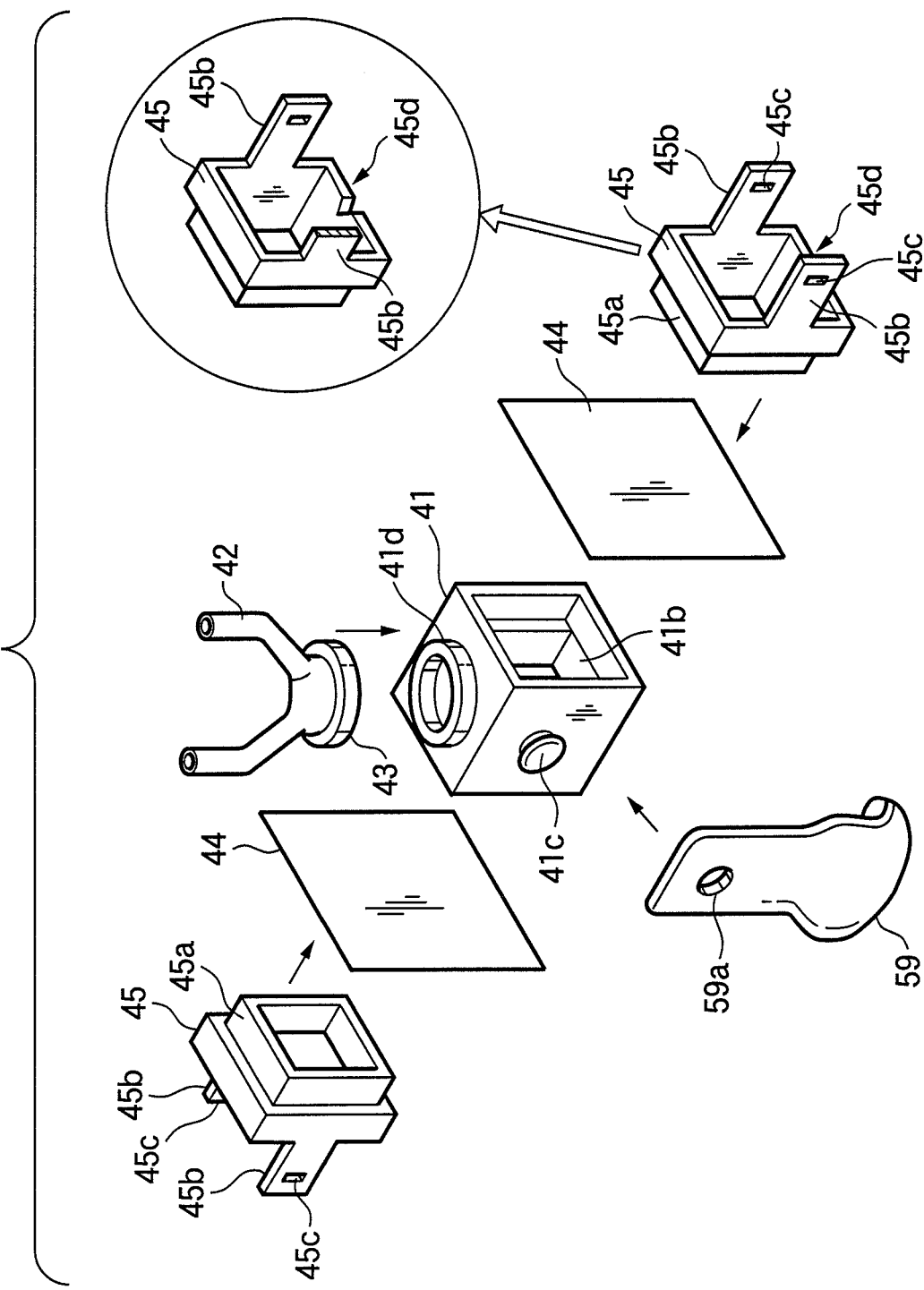
FIG. 14 is an exploded perspective view shown in part of FIG. 12.
Figure 15:
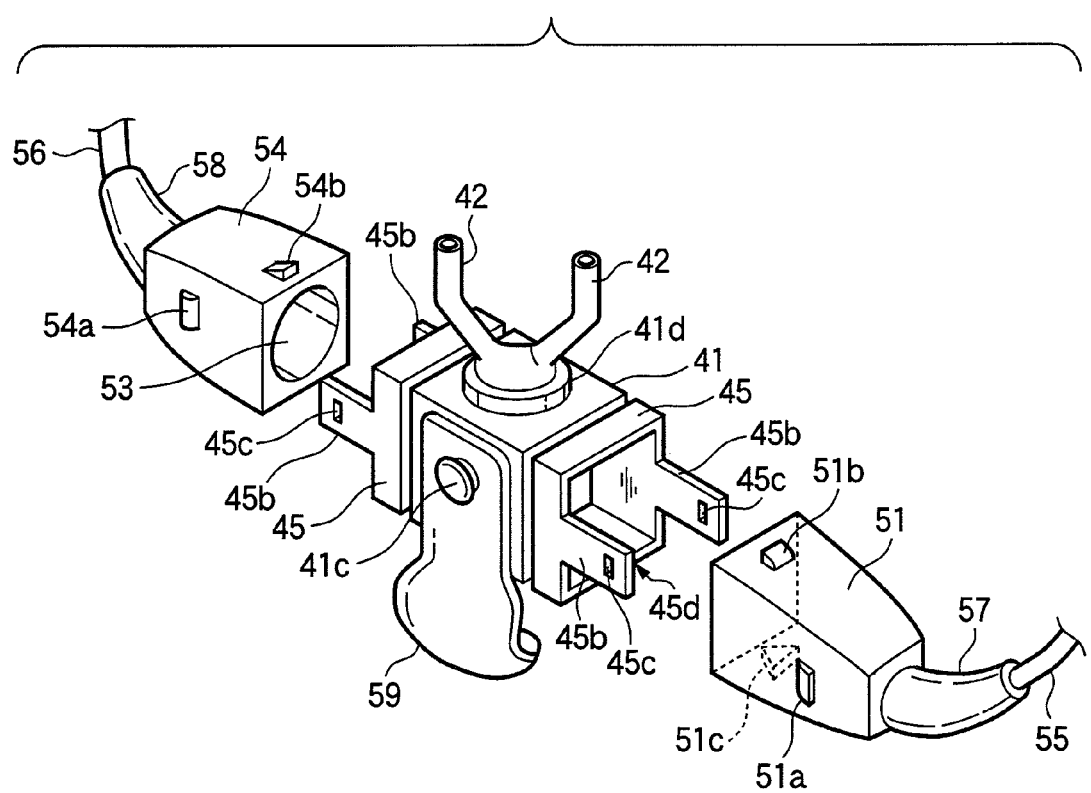
FIG. 15 is a perspective assembly view of the principal features shown in FIG. 12.
Figure 16:
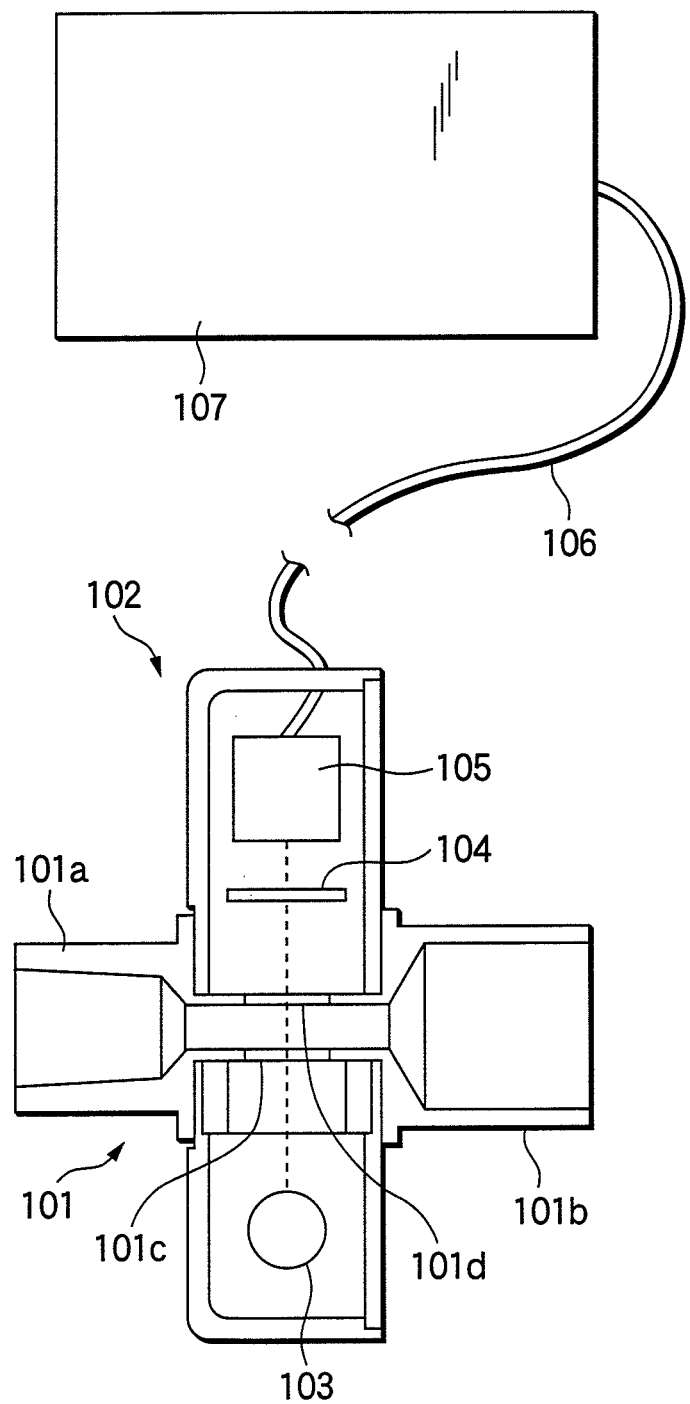
FIG. 16 is a descriptive view showing a schematic configuration of an example of a related capnometer for measuring the concentration of a carbon dioxide gas.
Figure 17:
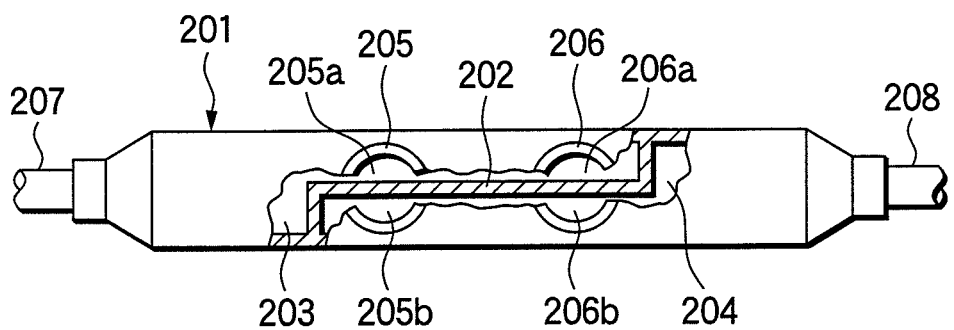
FIG. 17 is a longitudinal cross-sectional view showing an example configuration of a related-art nasal tube.
Figure 18:
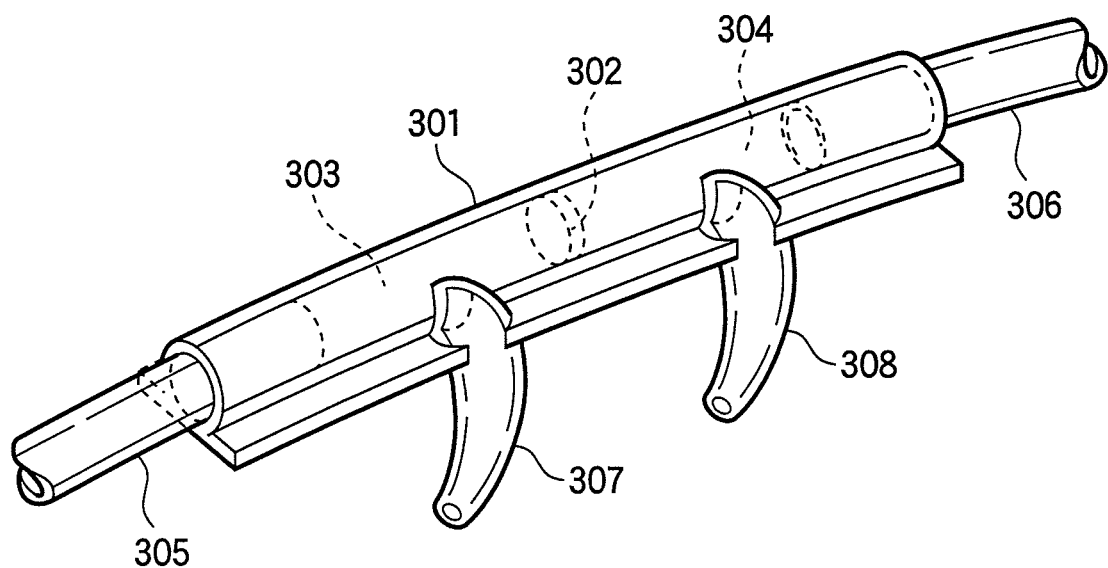
FIG. 18 is a perspective view showing another example configuration of the related-art nasal tube.

FIGS. 12 through 15 show examples of the third invention. FIG. 12 is a transverse cross-sectional view; FIG. 13 is a longitudinal cross-sectional view; FIG. 14 is an exploded perspective view; and FIG. 15 is a perspective assembly view of the principal features. As shown in these drawings, both lateral sides of an airway case 41 formed into a rectangular-parallelepiped shape are opened. A circular hole 41a is formed in the upper surface of the airway case 41 so that an adapter, which is thin circular shaped, to be described later is to be inserted into the hole. Further, a rectangular ventilating hole 41b is formed in the lower surface of the airway case 41. An adapter 43—on which two flexible nasal insertion prongs 42 made of, e.g., silicone rubber, are provided in an upright position—is fittingly attached to an adapter reception 41d provided on the upper surface of the airway case 41. Lower ends of the nasal prongs 42 are brought in communication with the inside of the airway case 41.

An anti-fogging film 44 which is a thin film is provided on each of the lateral sides of the airway case 41. A anti-fogging film case 45 is disposed outside of the each anti-fogging film 44 as a holding member. A step section 45a to be fitted into the inner periphery of one side of the air way case 41 is formed in an outer periphery at one end of the anti-fogging film case 45. The anti-fogging films 44 are pressed against the respective lateral sides of the airway case 41 by the anti-fogging film case 45. The steps 45a are fitted to the internal circumferences of the lateral sides so that the anti-fogging films 44 can be hermetically fastened to the airway case 41. A hook 41c—with which an air adapter for oral respiration to be described later is engaged—is provided on one side of the airway case 41.

Arms 45b are formed integrally with both sides of the anti-fogging film case 45 so as to project in the direction opposite to the step section 45a. An engagement hole 45c is formed in the vicinity of extremity of each arm 45b. A V-shaped notch 45d is formed in the center of the lower surface of the anti-fogging case 45 which opens in the same direction in which the arms 45b extend.

A light-emitting section 46 is attached to the outer side of one of the anti-fogging film cases 45, and a light-receiving section 47 is attached to the outer side of the remaining anti-fogging film case 45. The light-emitting section 46 is constituted of a rectangular-parallelepiped shaped light-emitting section case 51 serving as a support member for housing a light-emitting element 48, a reflecting mirror 49, and a window 50 made of sapphire in an aligned manner. Further, the light-receiving section 47 is constituted of a rectangular-parallelepiped shaped light-receiving section case 54 serving as a support member for housing a light-receiving element 52 and a window 53 made of sapphire in an aligned manner. A lead wire 55 connected to the light-emitting element 48 is led to the outside of the case 51 via a socket 57. Similarly, a lead wire 56 connected to the light-receiving element 52 is led to the outside of the case 54 via a socket 58.

A hook 51a is provided on either side surface of the light-emitting section case 51. A projection 51b is provided on the upper surface of the light-emitting section case 51. When the light-emitting section case 51 is fitted into the space defined between the arms 45b of the anti-fogging film case 45, the hook 51a is engaged with and locked by the engagement holes 45c formed in the respective arms 45b. The projection 51b provided on the upper surface of the light-emitting section case 51 is brought into contact with and positioned by the upper end face of the anti-fogging film case 45. Further, a triangular projection 51c is provided on the lower surface of the light-emitting section case 51. At the time of assembly, the projection 51c is engaged with and positioned by the notch 45d formed in the lower end face of the anti-fogging film case 45. A hook 54a and projections 54b, 54c, which operate in the same manner as the hook 51a and the projections 51b, 51c, are formed on the light-receiving section case 54.

An air guide for oral respiration 59 is removably attached to one side surface of the airway case 41. The air guide for oral respiration 59 is formed from, e.g., flexible polypropylene, into the shape of a spoon. A hole 59a is formed in an upper part of the air guide for oral respiration 59 so that the hook 41c formed on the airway case 41 is fitted to the hole.

According to this example, the light-emitting section case 51 and the light-receiving section case 54 are removably attached to the airway case 41. Hence, bonding of the windows 50, 53 made of sapphire to the corresponding cases 51, 54 is facilitated, thus improving productivity. Further, cleaning of the airway case 41 is also made easy.

The foregoing configuration example has described a case where respiratory gas from the nose is introduced to the airway case 41 via the nasal prongs 42. Alternatively, the adapter 43 having the nasal prongs 42 may be omitted, and respiratory gas may be introduced directly into the airway case 41. If the air guide for oral respiration 59 is not necessary, it may be omitted.

As has been described, a sensor for measuring the concentration or presence/absence of carbon dioxide in respiratory gas from a living body according to the present invention comprises a support member for supporting a light-emitting element and a light-receiving element which are disposed on a single optical axis so as to oppose each other; and a respiratory flow path which is formed in the support member and through which respiratory gas can flow so as to cross over the optical axis when the support member is attached to an area located below the nostrils or to an oxygen mask covering the face of the living body. Hence, an airway adapter and a sampling tube, which have hitherto been used, become unnecessary, thereby rendering the sensor compact and less-expensive. Further, measurement accuracy and response of the sensor are improved. Moreover, since the power consumed by the light-emitting element is made smaller, a temperature rise becomes smaller, thus obviating a risk of occurrence of a burn.

What is claimed is:

1. A sensor, adapted to be attached on a human body to measure concentration or presence/absence of carbon dioxide in respiratory gas from the human body, the sensor comprising:
   a light-emitting element, operable to emit light;
   a light-receiving element, configured to receive the light;
   a support member, supporting the light-emitting element and the light-receiving element, and configured to be brought into contact with a part between nostrils and a mouth of the human body when the sensor is attached on the human body; and a respiratory flow path formed in the support member and intersecting between the light-emitting element and the light-receiving element, the respiratory flow path being configured to allow the respiratory gas to pass therethrough when the support member is brought into contact with the part between the nostrils and the mouth, wherein a width of the support member in a direction perpendicular to a line extending between the light-emitting element and the light-receiving element is smaller than a distance between the nostrils and the mouth.

2. The sensor as set forth in claim 1, wherein the respiratory path is configured to allow the respiratory gas from the human body to pass between the light-emitting element and the light-receiving element and then to be out from the support member, when the support member is brought into contact with the part between the nostrils and the mouth.

3. The sensor as set forth in claim 1, further comprising an engagement member, provided on the support member and configured to be engaged with a tubular member for supplying oxygen to the nostrils.

4. The sensor as set forth in claim 1, further comprising a mouth-side guide member, provided on the support member and configured to guide respiratory gas from the mouth to the respiratory flow path when the sensor is attached to the human body.

5. The sensor as set forth in claim 1, further comprising a nasal-side guide member, configured to guide respiratory gas from the nostrils to the respiratory flow path when the sensor is attached to the human body.

6. The sensor as set forth in claim 5, wherein the nasal-side guide member has two nasal prongs configured to be inserted into the nostrils when the support member is brought into contact with the part between the nostrils and the mouth.

7. The sensor as set forth in claim 5, wherein the nasal-side guide member comprises a funnel-shaped member.

8. An airway case, adapted to be attached on a human body and adapted to support a light-emitting element and a light-receiving element to measure concentration or presence/absence of carbon dioxide in respiratory gas from the human body, the airway case comprising:

a support member, having a first part configured to support the light-emitting element and a second part configured to support the light-receiving element, the support member being configured to be brought into contact with a part between nostrils and a mouth of the human body when the airway case is attached on the human body; and a respiratory flow path formed in the support member and intersecting between the first part and the second part, the respiratory flow path being configured to allow the respiratory gas to pass therethrough when the support member is brought into contact with the part between the nostrils and the mouth, wherein a width of the support member in a direction perpendicular to a line extending between the light-emitting element and the light-receiving element is smaller than a distance between the nostrils and the mouth.

9. The airway case as set forth in claim 8, wherein the respiratory path is configured to allow the respiratory gas from the human body to pass between the light-emitting element and the light-receiving element and then to be out from the support member, when the support member is brought into contact with the part between the nostrils and the mouth.

10. The airway case as set forth in claim 8, further comprising an engagement member, provided on the support member and configured to be engaged with a tubular member for supplying oxygen to the nostrils.

11. The airway case as set forth in claim 8, further comprising a mouth-side guide member, provided on the support member and configured to guide respiratory gas from the mouth to the respiratory flow path when the airway case is attached to the human body.

12. The airway case as set forth in claim 8, further comprising a nasal-side guide member, configured to guide respiratory gas from the nostrils to the respiratory flow path when the airway case is attached to the human body.

13. The airway case as set forth in claim 12, wherein the nasal-side guide member has two nasal prongs configured to be inserted into the nostrils when the support member is brought into contact with the part between the nostrils and the mouth.

14. The airway case as set forth in claim 12, wherein the nasal-side guide member comprises a funnel-shaped member.

15. The sensor as set forth in claim 1, wherein the support member further comprises a first housing portion and a second housing portion, the first housing portion enclosing the light-emitting element and the second housing portion enclosing the light-receiving element, the first housing portion and the second housing portion are connected by a connecting member extending between the first housing portion and the second housing portion and that is connected to a back side of each of the first housing portion and the second housing portion, and a volume defined by the first housing portion, the second housing portion and the connecting member is externally open to receive respiratory air from a top side, a bottom side and a front side of the volume.

16. The airway case as set forth in claim 8, wherein the first part and the second part are connected by a connecting member extending between the first part and the second part, the connecting member is connected to a back side of each of the first part and the second part, and a volume defined by the first part, the second part and the connecting member is externally open to receive respiratory air from a top side, a bottom side and a front side of the volume.

17. The sensor as set forth in claim 1, wherein the support member has a length longer than a width, and the width of the support member is configured to fit between the nostrils and the mouth.

18. The airway case as set forth in claim 8, wherein the support member has a length longer than a width, and the width of the support member is configured to fit between the nostrils and the mouth.

\* \* \* \* \*